United States Patent [19]

Schneider et al.

[11] Patent Number: 4,801,738

[45] Date of Patent: Jan. 31, 1989

[54] PREPARATION OF δ-FORMYLVALERATES

[75] Inventors: Heinz-Walter Schneider, Ludwigshafen; Rudolf Kummer, Frankenthal; Volker Taglieber, Eppelheim, all of Fed. Rep. of Germany

[73] Assignee: BASF Aktiengesellschaft, Ludwigshafen, Fed. Rep. of Germany

[21] Appl. No.: 608,460

[22] Filed: May 9, 1984

[30] Foreign Application Priority Data

May 11, 1983 [DE] Fed. Rep. of Germany ....... 3317164

[51] Int. Cl.$^4$ ...................... C07C 67/38; C07C 69/67
[52] U.S. Cl. .................................... 560/177; 560/179; 560/205; 560/265
[58] Field of Search ............................... 560/177, 175

[56] References Cited

U.S. PATENT DOCUMENTS

| | | | |
|---|---|---|---|
| 3,253,018 | 5/1966 | Zachry et al. | 560/177 |
| 3,527,809 | 9/1970 | Pruett et al. | 560/177 |
| 3,697,580 | 10/1972 | Overwein et al. | 560/261 |
| 4,360,692 | 11/1982 | Kummer et al. | 560/175 |

FOREIGN PATENT DOCUMENTS 1586805  3/1981  United Kingdom .

OTHER PUBLICATIONS

Bull. Chem. Soc. of Japan, Band 46, S.528, Akio Matsudo.

*Primary Examiner*—Vivian Garner
*Attorney, Agent, or Firm*—Keil & Weinkauf

[57] ABSTRACT

δ-Formylvalerates are prepared by a process wherein a 3-pentenoate is treated with an isomerization catalyst at elevated temperatures and a 4-pentenoate is distilled off, and the resulting 4-pentenoate is reacted with carbon monoxide and hydrogen at from 80 to 160° C. under from 1 to 30 bar in the presence of a rhodium carbonyl complex which has been modified with tertiary organic phosphines or phosphites.

4 Claims, No Drawings

PREPARATION OF δ-FORMYLVALERATES

Bull. Chem. Soc. Japan, Volume 46, page 528 and U.S. Pat. No. 3,253,018 disclose that δ-formylvalerates are obtained by hydroformylation of a pentenoate in the presence of a cobalt carbonyl catalyst. However, this procedure gives substantial amounts of branched esters, which are undesirable with regard to further use. Attempts have also been made to isomerize the 3-pentenoate, which is the main component of the mixture of pentenoates, to give the 4-pentenoate. However, Bull. Chem. Soc. Japan, Volume 46, page 528 states that the isomerization of 3-pentenoates with cobalt carbonyl gives mainly 2-pentenoates.

When thermodynamic equilibrium is reached in the isomerization of a 3-pentenoate, 5 isomers, i.e., the 4-pentenoate, the cis- and trans-3-pentenoates and the cis- and trans-2-pentenoates, are present, the equilibrium being shifted markedly toward the trans-2-pentenoate.

It is an object of the present invention to design the hydroformylation of pentenoates so that a very small amount of branched compounds is formed, and to isomerize 3-pentenoates so that essentially the double bond shifts linearly to give 4-pentenoates, and the amounts of cis-2-pentenoates produced are kept to a minimum, these compounds being difficult to separate off.

We have found that this object is achieved by a process for the preparation of δ-formylvalerates by reacting a pentenoate with carbon monoxide and hydrogen under superatmospheric pressure and at elevated temperatures in the presence of a carbonyl complex of a metal of group 8 of the periodic table, wherein (a) a 3-pentenoate is treated with an isomerization catalyst at elevated temperatures and a 4-pentenoate is distilled off from the reaction mixture, and (b) the resulting 4-pentenoate is reacted with carbon monoxide and hydrogen at from 180° to 160° C. and under from 1 to 30 bar in the presence of a rhodium carbonyl complex which has been modified with tertiary organic phosphines or phosphites.

The novel process has the advantage that, in the isomerization of 3-pentenoates, only a small amount of cis-2-pentenoates, which are difficult to separate off, is formed, and the catalyst has a long life. Another advantage of the novel process is that δ-formylvalerates can be prepared by a procedure in which only minor amounts of branched compounds are produced.

The novel process is remarkable in that, according to U.S. Pat. No. 3,253,018, rhodium catalysts are unsuitable for the preparation of δ-formylvalerates by hydroformylation of pentenoates, since these catalysts result essentially in the formation of branched aldehydes.

Preferred starting materials are 3-pentenoates derived from alcohols of not more than 12 carbon atoms.

Alkyl 3-pentenoates, in particular those obtained with alcohols of 1 to 4 carbon atoms, are particularly preferred. Examples of suitable 3-pentenoates are methyl 3-pentenoate, ethyl 3-pentenoate and butyl 3-pentenoate.

The 3-pentenoate is treated with an isomerization catalyst, for example an acidic ion exchanger, an acidic zeolite, cobalt carbonyl or a modified rhodium triphenylphosphine complex.

It is preferable to use strongly acidic ion exchangers, for example crosslinked polystyrenes containing acidic groups, in particular sulfonic acid groups and styrene/divinyl benzene copolymers containing sulfonic acid groups have proven particularly useful. Preferred zeolites are A, X and Y zeolites in their H, i.e., acidic, form. The acidic ion exchangers and acidic zeolites contain a noble metal of group 8 of the periodic table, in particular palladium, rhodium or ruthenium, particularly preferably palladium, advantageously in an amount of from 0.01 to 1% by weight.

The isomerization is carried out at elevated temperatures, advantageously at from 80° to 180° C. Where acidic ion exchangers are used, temperatures of from 80° to 140° C. have proven suitable. The isomerization is advantageously carried out at the boiling point, under the pressure used, of the particular 4-pentenoate formed. As a rule, it is carried out under atmospheric pressure, but it is also possible to use reduced pressure or slightly superatmospheric pressure, e.g., not more than 2 bar.

The residence time is advantageously from 0.05 to 1 hour. The 4-pentenoate is distilled off from the reaction mixture, and the remaining mixture is advantageously fed once again to the isomerization.

The 4-pentenoate thus obtained is reacted with carbon monoxide and hydrogen. As a rule, the gas mixture contains carbon monoxide and hydrogen in a molar ratio of from 4:1 to 1:4. Advantageously, the mixture used contains about equimolar amounts of carbon monoxide and hydrogen. The said gas mixture is used, as a rule, in a stoichiometric amount or in an excess of up to 20%, based on the 4-pentenoate.

The hydroformylation is carried out at from 80° to 140° C., advantageously from 90° to 120° C., and under from 1 to 30, advantageously from 8 to 20, bar.

The reaction is carried out in the presence of a rhodium carbonyl complex which has been modified with tertiary organic phosphines or phosphites. Advantageously used modifiers are tertiary organic phosphines which contain hydrocarbon radicals as substituents. Preferred substituents are alkyl of not more than 18 carbon atoms, cycloalkyl of 5 to 12 carbon atoms, aralkyl of 7 to 10 carbon atoms and aryl, in particular phenyl. The radicals may be identical or different.

Triphenylphosphine and alkyldiphenylphosphines have become particularly important. Examples of suitable phosphines are triphenylphosphine, hexyldiphenylphosphine and substituted arylphosphines, such as tritolylphosphine.

The tertiary phosphines are advantageously used in amounts such that the atomic ratio of rhodium to phosphorus is from 1:1 to 1:1,000, in particular from 1:5 to 1:300. Rhodium is preferably used in an amount of from 0.01 to 1% by weight, calculated as metal and based on the 4-pentenoate used. The catalyst can be prepared before the reaction. The procedure advantageously employed in industry is to produce the catalyst in situ, during the reaction, from the individual components, for example a rhodium salt, carbon monoxide and the stated tertiary organic phosphines.

The δ-formylvalerates produced can be isolated from the reaction mixture, for example by distillation.

The δ-formylvalerates obtainable by the process of the invention are useful for the preparation of caprolactam, hexanediol and adipic acid.

The Example which follows illustrates the process according to the invention.

EXAMPLE 100 g of a mixture of 70% by weight of methyl trans-3-pentenoate and 30% by weight of methyl cis-3-pentenoate, as obtained in the carbonylation of buta-1,3-diene, with 10 g of a catalyst of the Y zeolite type laden with 0.5% of palladium are stirred at 135° C. in a glass flask. After a reaction time of 6 minutes, the reaction mixture obtained is composed of 8% by weight of the 4-pentenoate, 0.1% by weight of the cis-2-pentenoate, 64.3% by weight of the trans-3-pentenoate, 27.4% by weight of the cis-3-pentenoate and 0.2% by weight of the trans-2-pentenoate. The catalyst productivity is 26.6 g of methyl 4-pentenoate per g of Pd per minute of reaction time.

After the catalyst has been separated off, the reaction mixture is distilled in a column possessing 100 separation stages, the reflux ratio being 50. 8.2 g of 95% pure methyl 4-pentenoate are taken off at a top temperature of 126° C. The bottom product from the distillation (91.8 g) is supplemented by 8.2 g of the 3-pentenoate mixture of the above composition and is then used once again for the isomerization.

180 g of the methyl pentenoate mixture which is obtained by this process and contains 171 g (1.5 moles) of methyl 4-pentenoate are subjected to hydroformylation in 300 g of toluene as a solvent, the procedure being carried out in a 1 liter lift-type stirred autoclave. The reaction mixture contains 35.1 g (134 millimoles) of triphenylphosphine and 54 mg (0.52 millimole) of rhodium in the form of the complex $HRhCOL_3$ (L=$PPh_3$) as the catalyst, and is heated to 110° C., after which the pressure is brought to 8 bar with a mixture of 80 vol% of $H_2$ and 20 vol% of CO. If, during the reaction, the pressure in the reactor falls below 7 bar, it is increased to 8 bar once again by forcing in an equimolar mixture of $H_2$ and CO. After a reaction time of 2 hours, analysis of the reaction mixture shows that the methyl 4-pentenoate has been converted as follows:

| | |
|---|---|
| Unreacted 4-pentenoate | 8.0 mol % |
| 3-Pentenoate and 2-pentenoate | 10.5 mol % |
| Methyl valerate | 2.6 mol % |
| δ-Formylvalerate | 71.8 mol % |
| γ-Formylvalerate | 6.2 mol % |
| Hydroxycaproate | 0.5 mol % |
| Other by products | 0.4 mol % |

The ratio of δ-formylvalerate to γ-formylvalerate is 92:8, and the yield of the actual desired product, ie. the δ-formylvalerate, is 78%.

Since, however, both the unreacted 4-pentenoate and the 3- and 2-isomers formed can once again be converted to the 4-pentenoate and then used again for the hydroformylation, the critical factor with regard to cost-efficiency is the selectivity, ie. the molar amount of δ-formylvalerate produced per mole of pentenoate consumed; this selectivity is 88%.

We claim:
1. A process for the preparation of δ-formylvaleric acid esters of an alcohol of not more than 12 carbon atoms, wherein
    (a) a 3-pentenoic acid ester of an alcohol of not more than 12 carbon atoms is isomerized by treating it with an acidic ion exchanger or acidic zeolite containing palladium, rhodium or ruthenium at from 80° to 180° C. and a 4-pentenoic acid ester of an alcohol of not more than 12 carbon atoms is distilled off from the reaction mixture, and
    (b) the resulting 4-pentenoic acid ester of an alcohol of not more than 12 carbon atoms is reacted with carbon monoxide and hydrogen at from 80° to 160° C. and under from 1 to 30 bar in the presence of a rhodium carbonyl complex which has been modified with tertiary organic phosphines or phosphites.
2. A process as set forth in claim 1, wherein the acidic ion exchanger or acidic zeolite contains from 0.01 to 1% by weight of palladium, ruthenium or rhodium.
3. A process as set forth in claim 1, wherein the residence time in the isomerization of the 3-pentenoate is from 0.05 to 1 hour.
4. A process as set forth in claim 1, wherein a 4-pentenoate is reacted with carbon monoxide and hydrogen in the presence of a rhodium carbonyl complex which has been modified with triphenylphosphine.

* * * * *